US00PP22413P2

(12) United States Plant Patent
Asch

(10) Patent No.: US PP22,413 P2
(45) Date of Patent: Dec. 27, 2011

(54) ***HOSTA* PLANT NAMED 'SEDUCER'**

(50) Latin Name: *Hosta hybrid (Tratt.)*
Varietal Denomination: Seducer

(76) Inventor: Stuart Asch, Clawson, MI (US)

( * ) Notice: Subject to any disclaimer, the term of this patent is extended or adjusted under 35 U.S.C. 154(b) by 0 days.

(21) Appl. No.: 12/804,451

(22) Filed: Jul. 22, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Kent L Bell

(57) ABSTRACT

A new and distinct *Hosta* plant named 'Seducer' characterized by cordate leaves having variegated leaf margins of yellowish green, leaf centers of bluish dark green center and developing an irregular thin creamy white intermediate bolt between the margin and center, with near white flowers and light lavender buds on strong erect scapes.

1 Drawing Sheet

Botanical classification: *Hosta* hybrid (Tratt.)
Variety denomination: 'Seducer'.

BACKGROUND AND ORIGIN OF THE PLANT

The present invention relates to the new and distinct *hosta* plant, *Hosta* 'Seducer' hybridized by Stuart R. Asch in the summer of 1997 at a garden in Clawson, Mich. and was separated as a seedling of potential in the summer of 2001. The new plant is the result of an open-pollination between *Hosta* 'Dorothy Benedict' (not patented) as the female or pod parent and an unknown plant as the male or pollen parent. *Hosta* 'Seducer' has been asexually propagated by division at the garden in Clawson, Mich. and has also been propagated by tissue culture at a nursery in Zeeland, Mich. since the fall of 2006 with all resultant asexually propagated plants having retained all the same traits as the original plant. The plant is stable and reproduces true to type in successive generations of asexual reproduction.

The most similar known *hosta* cultivar known to the applicant is: *Hosta* 'Déjà Blu' (not patented). 'Déjà Blu' has a similar white bolting between the yellow margin and bluish green center. However, the new plant has a much larger leaf and larger habit, has less lavender in the flowers and blooms later that 'Déjà Blu'. *Hosta* 'Seducer' differs from its female parent by having a stable variegated leaf margin compared to an unstable streaking throughout the leaf, more cordate leaf blades with less rugose and a taller flower scape with slightly more lavender buds.

*Hosta* 'Seducer' differs from all other *hostas* known to the applicant, by the combination of the following traits.

1. Cordate leaf blades with yellowish green margin a bluish dark green center.
2. Developing a thin creamy white bolt irregularly flashing and following the jetting between the margin and center colors.
3. Lavender buds opening to near white flowers beginning in late June.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
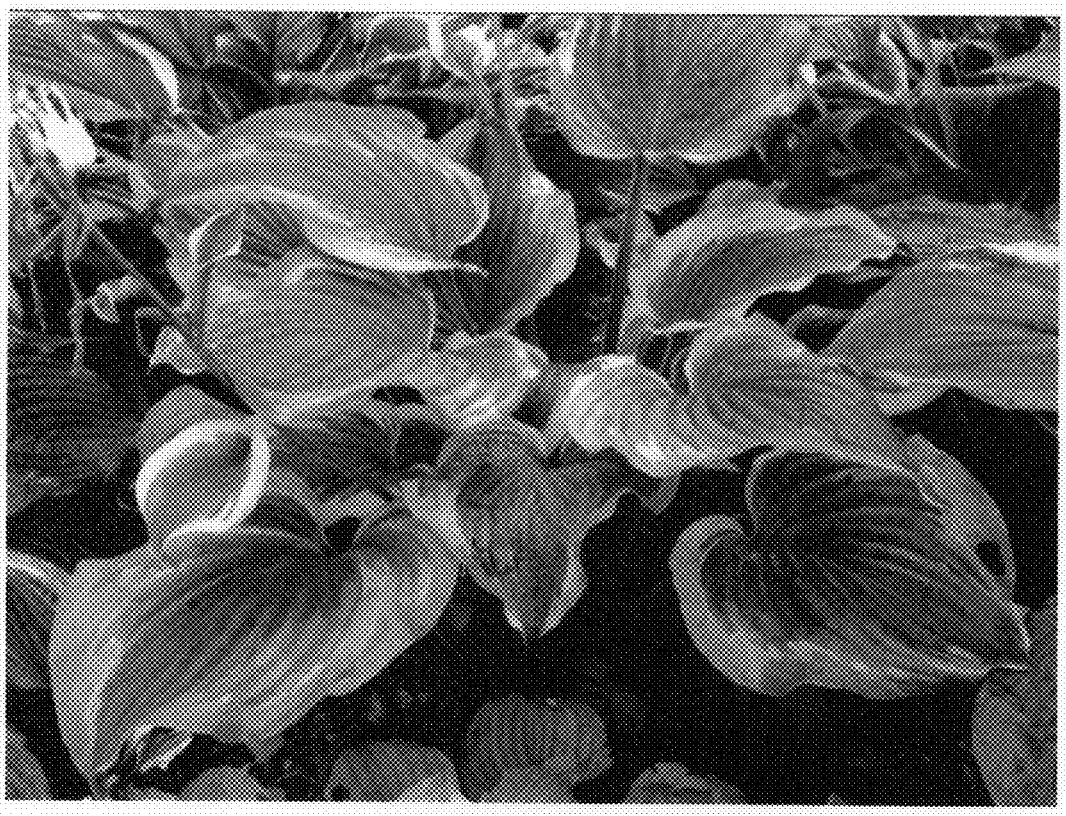
FIG. 1 shows the habit of the new plant in mid season in the landscape.
Figure 2:
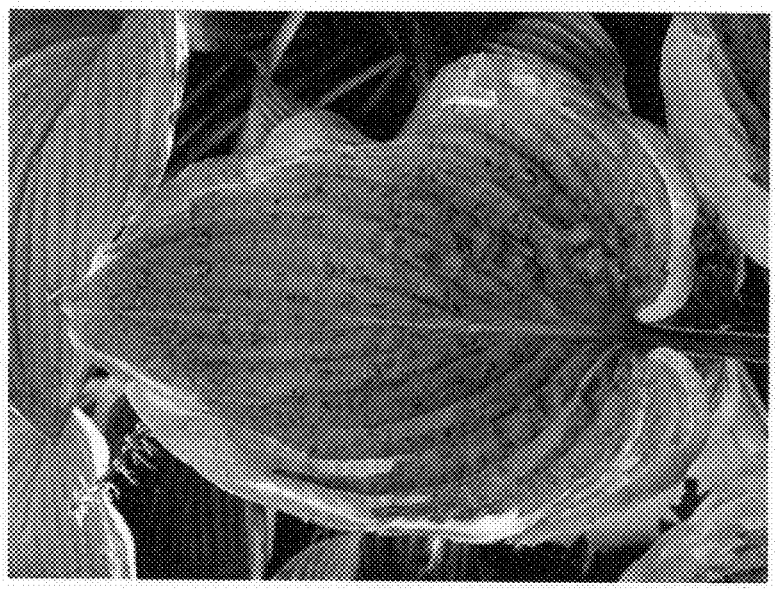
FIG. 2 shows a close-up of a leaf of the new plant in mid season.

The following descriptions and color references are based on the 2001 edition of The Royal Horticultural Society Colour Chart except where common dictionary terms are used. The new plant, *Hosta* 'Seducer', has not been observed under all possible environments. The phenotype may vary slightly with different environmental conditions, such as temperature, light, fertility, moisture and maturity levels, but without any change in the genotype. The following observations and size descriptions are of a three-year old plant in a 50% shaded trial garden in Zeeland, Mich. with supplemental water and fertilizer.

Botanical classification: *Hosta* hybrid;

Parentage: Female—*Hosta* 'Dorothy Benedict' (not patented); male—unknown;

Propagation: Garden division and sterile plant tissue culture;

Time to initiate roots from tissue culture: About two to three weeks;

Growth rate: Moderate;

Crop time: About 12 to 15 weeks to finish during the summer in a one-liter container from rooted tissue culture plantlet;

Rooting habit: Fleshy, lightly branching, with roots up to 35 cm long;

Plant shape and habit: Hardy herbaceous perennial with basal rosette of leaves emerging from rhizomes producing a symmetrical mound of semi horizontal leaves in youth, becoming slightly more rounded with age; producing upright flowering scapes;

Plant size: Foliage height about 45 cm tall from soil line to the top of the leaves and about 110 cm wide at the widest point just above soil line;

Foliage description: Entire, glabrous, glaucous, cordate, acute leaf apex with cordate to auriculate base; coarsely rippled undulation along margin; 20 to 28 cm long and 16 to 22 cm wide, average 22 cm long and 18 cm wide;

Leaf blades: Simple, entire, with undulated margin; bi-laterally symmetrical; glabrous and dull surface on top, glabrous and glaucous below; variegation pattern variable with the margin between about 2.5 cm to 4.0 cm wide with some jetting of margin or center color into the edge or center and uneven folding of the tunic layers producing a series of intermediate colors between the leaf center and margin;

Leaf blade color: Early season adaxial (top) center color closest to RHS 137D; early season abaxial (underside) center closest to RHS N138D; early season margin adaxial closest to RHS 144A; early season abaxial margin closest to RHS 144D; Mid-season and later summer adaxial margins between RHS N144A and RHS 153A; mid-season and later summer abaxial margins closest to RHS 153A; mid-season and later center closest to RHS 139B and abaxial center nearest RHS N138D; intermediate colors where margin and center unevenly fold of RHS 148C, RHS 147D, RHS 138D and also with an irregular bolt of RHS 11D between margin and the next color inside of the margin;

Petiole: Entire, glabrous; mostly straight from base of plant to leaf base, concave center, slightly stiff; 27 to 35 cm long and 14 to 20 mm wide at base, average about 30 cm long and 18 mm wide;

Petiole color: Adaxial center closest to RHS 138A with adaxial margin closest to RHS 12D; abaxial center pale green between RHS 145B and RHS 145C darkening to slightly darker than RHS 145A with abaxial margin closest RHS 12D;

Veins: Parallel, slightly raised on abaxial side, 12 pair;

Veins color: Adaxial side closest to RHS 144B and abaxial side between RHS 138B and RHS 138C;

Flower description:

*Buds two to three days prior to opening.*—Globose apex about 1.4 cm in diameter with base narrowing at about mid-length to about 0.4 cm diameter; about 4.0 cm long.

*Bud color.*—White near base lighter than RHS 155D and lavender between RHS 84C and RHS 84D near apex with the apical 2 mm green closest to RHS 138A.

*Flowers.*—Funnelform; 3.5 to 4.0 cm wide and 6.0 to 6.5 cm long, (distal flowers smaller), persists for a normal period, usually one day on plant or as cut flower; stapes remain effective with flowers from late June to late July with 35 to 50 flowers per scape; no detectable fragrance.

*Tepal.*—Two sets of three, fused at base; clavate with acute apex; glabrous, entire; each approximately 6.0 cm long and the inner set 1.5 cm wide and outer set 1.3 cm wide; coloring of both sets identical, white, lighter than RHS 155D, inside and out with slight tinting of RHS 84C near apical 3 mm of outer tepal set; tepal veins distinctly depressed set of seven on adaxial surface of outer tepals with inner tepals only three depressed veins; vein color white, lighter than RHS 155D.

*Gynoecium.*—Style: single, 6.5 to 7.0 cm long, 1 mm diameter, curled upward at distal end; RHS 11D. Stigma: single; globose, about 2 mm in diameter, RHS 157A. Ovary: oblong, about 7.0 mm long and 2.5 mm wide; color between RHS 145A and RHS 145B.

*Androecium.*—Filaments: six, less than 1 mm in diameter and 3.0 cm long curved upward in the apical 0.5 cm; closest to RHS 11D. Anthers: 4 to 5 mm long, 1.5 mm wide, dehiscent longitudinally; closest to RHS N187C. Pollen: elliptic, less than 0.1 mm long, closest to RHS 13B.

*Peduncle.*—One per mature division; glaucous; 85 to 90 degrees from horizontal, more horizontal with more single directional lighting; 90 to 100 cm tall, and up to 10 mm in diameter at base; closest to RHS 138A with a heavy glaucous bloom.

*Pedicel.*—Approximately 15 mm long, 2 mm wide; RHS 141B at base and closest to RHS 157D at distal portion, becoming RHS 138A with ripening fruit.

*Bracts.*—Each flower subtended by a single bract decreasing in size distally with one or two additional bracts about 4.0 cm and 16.0 cm below first flower; glaucous and glabrous both surfaces, margin entire, sessile, apex acute; concaved supporting flower bud; lowest bracts resembling sessile leaves with largest 13.5 cm long 6.5 cm wide and smallest bracts 1.0 cm long and about 0.5 cm wide.

*Bract color.*—Lower bracts center closest to RHS 138A adaxial and abaxial surfaces; adaxial margins closest to RHS 11A; abaxial margins nearest RHS 11B; intermediate colors between margins and center ranging closest to RHS 145C and RHS 138D; upper bracts adaxial and abaxial surfaces between RHS 189A and RHS 137B with purplish tinting of closest to N187B and 1 mm wide margins of RHS 159D with tinting of RHS N187D.

Fruit: Tri-loculicidal capsule, about 3.5 cm long and 7 mm diameter; between RHS 139B and RHS 141B as ripening;

Seed: Flattened single-winged nutlet with swollen embryo at one end; about 12 mm long, 3 mm wide and 1 mm thick at embryo; nearest RHS 202A;

Disease and pest resistance: The new plant has not shown any resistance to pests and diseases common to *hostas*. The plant grows best and shows best coloration with plenty of moisture, adequate drainage and light shade, but is able to tolerate some drought when mature and direct sun without leaf burn when provided sufficient water. Hardiness at least from USDA zone 3 through 9, and other disease resistance is typical of that of other *hostas*.

I claim:

1. A new and distinct cultivar of ornamental *Hosta* plant named 'Seducer' as herein described and illustrated, with wide variegated leaf margins of yellowish green, leaf centers of bluish dark green center and developing an irregular thin creamy white intermediate bolt between the margin and center, with near white flowers and light lavender buds on strong erect scapes suitable as a potted plant, for the garden, and for cut flower arrangements.

* * * * *